United States Patent
Hakata et al.

(10) Patent No.: US 9,127,168 B2
(45) Date of Patent: Sep. 8, 2015

(54) MAGNETIC IRON OXIDE FINE PARTICLES, AND MAGNETIC PARTICLE-CONTAINING WATER DISPERSION AND PROCESS FOR PRODUCING THE SAME

(71) Applicant: TODA KOGYO CORPORATION, Otake-shi, Hiroshima-ken (JP)

(72) Inventors: Toshiyuki Hakata, Otake (JP); Tomoko Okita, Otake (JP)

(73) Assignee: TODA KOGYO CORPORATION, Otake (JP)

( * ) Notice: Subject to any disclaimer, the term of this patent is extended or adjusted under 35 U.S.C. 154(b) by 0 days.

(21) Appl. No.: 14/631,353

(22) Filed: Feb. 25, 2015

(65) Prior Publication Data

US 2015/0164803 A1    Jun. 18, 2015

Related U.S. Application Data

(62) Division of application No. 13/510,651, filed as application No. PCT/JP2010/070555 on Nov. 18, 2010, now abandoned.

(30) Foreign Application Priority Data

Nov. 20, 2009 (JP) ................. 2009-265469

(51) Int. Cl.
| | |
|---|---|
| C09C 1/24 | (2006.01) |
| A61K 47/48 | (2006.01) |
| B82Y 30/00 | (2011.01) |
| C01G 49/08 | (2006.01) |
| A61K 41/00 | (2006.01) |
| A61K 49/00 | (2006.01) |
| B82Y 5/00 | (2011.01) |
| A61K 47/04 | (2006.01) |
| A61K 49/04 | (2006.01) |
| A61K 49/18 | (2006.01) |

(52) U.S. Cl.
CPC .............. *C09C 1/24* (2013.01); *A61K 41/0052* (2013.01); *A61K 47/48861* (2013.01); *A61K 47/48884* (2013.01); *A61K 49/0002* (2013.01); *A61K 49/0428* (2013.01); *A61K 49/1854* (2013.01); *B82Y 5/00* (2013.01); *B82Y 30/00* (2013.01); *C01G 49/08* (2013.01)

(58) Field of Classification Search
None
See application file for complete search history.

(56) References Cited

U.S. PATENT DOCUMENTS

| 2005/0084539 A1 | 4/2005 | Handa et al. |
| 2006/0287404 A1 | 12/2006 | Horiishi et al. |

FOREIGN PATENT DOCUMENTS

| JP | 64-004002 | 1/1989 |
| JP | 64-049206 | 2/1989 |
| JP | 03-128331 | 5/1991 |
| JP | 04-052202 | 2/1992 |
| JP | 05-310429 | 11/1993 |
| JP | 07-122410 | 5/1995 |
| JP | 8-500700 | 1/1996 |
| JP | 11-106391 | 4/1999 |
| JP | 2003-112925 | 4/2003 |
| JP | 2006-028032 | 2/2006 |
| JP | 2007-023027 | 2/2007 |
| JP | 4079996 | 4/2008 |
| JP | 2008-111703 | 5/2008 |
| WO | WO 95/31220 | 11/1995 |
| WO | WO 03/066644 | 8/2003 |

OTHER PUBLICATIONS

'International Search Report for PCT/JP2010/070555, mailed Dec. 2010.
In et al., "Preparation and properties of poly(acrylic acid) oligomer stabilized superparamagnetic ferrofluid", *Journal of Colloid and Interface Science*, vol. 291, 2005, pp. 411-420.

*Primary Examiner* — Trevor Love
(74) *Attorney, Agent, or Firm* — Nixon & Vanderhye P.C.

(57) ABSTRACT

The present invention relates to a magnetic particle-containing water dispersion wherein the magnetic particles have a primary particle diameter of 5 to 15 nm and an average secondary particle diameter of 10 to 60 nm, and the water dispersion has a zeta potential of not more than −20 mV when a pH value of the water dispersion lies within the range of 6 to 8, and further a surface of the respective magnetic particles is coated with a carboxyl group-containing polymer. The magnetic particle-containing water dispersion is produced by heating an aqueous solution in which the carboxyl group-containing polymer is dissolved, to a temperature of 90 to 100° C. in a nitrogen atmosphere; adding a solution of a ferrous (II) salt and a ferric (III) salt and an alkali solution to the aqueous solution to react with each other at the same temperature; adding ethanol to the solution to obtain a precipitate; and removing a supernatant liquid from the solution, and then dispersing the precipitate in water and subjecting the resulting dispersion to dialysis. The magnetic particle-containing water dispersion is useful as a magnetic particle-containing water dispersion capable of producing magnetic particle-containing drugs for diagnosis and therapies which can exhibit a uniform functionality, with a good reproducibility.

3 Claims, No Drawings

MAGNETIC IRON OXIDE FINE PARTICLES, AND MAGNETIC PARTICLE-CONTAINING WATER DISPERSION AND PROCESS FOR PRODUCING THE SAME

This application is a Divisional of U.S. application Ser. No. 13/510,651, filed May 18, 2012, which is the U.S. national phase of International Application No. PCT/JP2010/070555, filed Nov. 18, 2010, which designated the U.S. and claims priority to JP Patent Application No. 2009-265469 filed Nov. 20, 2009, the entire contents of each of which are hereby incorporated by reference.

TECHNICAL FIELD

The present invention relates to a raw drug for magnetic particle-containing drugs which are used in drug delivery systems (hereinafter referred to merely as "DDS") as a method for delivering drugs, CT (computed tomography) diagnosis used for roentgen or MRI (magnetic resonance imaging system), and various therapies such as thermotherapy. More specifically, the present invention relates to a raw drug for magnetic particle-containing drugs which aims at improving delivery directivity of the magnetic particle-containing drugs to lesioned tissues and cells, contrast sensitivity in CT diagnosis and heat generation upon thermotherapy, etc.

BACKGROUND ART

In recent years, intensive studies have been made on the magnetic particle-containing drugs in the form of a composite material comprising magnetic iron oxide fine particles as a magnetic material and a biocompatible substance such as phospholipids, proteins and water-soluble polymers (Patent Documents 1 to 5, etc.).

In addition, in order to prepare a monodisperse aqueous solution of the magnetic iron oxide fine particles, there are known a method of coating a surface of the respective particles with a surface-treating agent such as surfactants (Patent Document 6); a method of coating a surface of the respective particles with an inorganic material such as Al and Si (Patent Document 7); a method of coating a surface of the respective particles with an organic metal polymer (Patent Document 4); a method of preparing the monodisperse aqueous solution without using any dispersant (Patent Document 8), etc.; or the like.

Further, it has been reported that in order to facilitate bonding between the magnetic iron oxide particles and vital molecules, the surface of the respective magnetic iron oxide particles is coated with a surface-modifying molecule having a functional group such as an amino group, a carboxyl group and a sulfone group (Patent Documents 9 to 11).

In any of these conventional arts, after once preparing an aqueous sol of iron oxide, the aqueous sol is mixed with respective polymers or polysaccharides. For this reason, the resulting magnetic particles have a large particle diameter owing to aggregation thereof, or these magnetic particles are merely weakly bonded to the surface-modifying molecule so that they tend to be readily dissociated from each other in blood and deteriorated in stability upon heat sterilization and stability with time.

In particular, the fine magnetic iron oxide particles may hardly be uniformly dispersed in the biocompatible substance and supported thereon owing to occurrence of excessive magnetic aggregation between the iron oxide particles. For this reason, the conventional magnetic iron oxide particles used for this purpose inevitably have a large particle diameter.

Also, there is a high possibility that the magnetic iron oxide particles having a large particle diameter remain in vivo after therapies. In addition, the magnetic iron oxide particles remaining in vivo may cause side reactions such as allergy reaction. Thus, the conventional magnetic iron oxide particles have failed to ensure a sufficient safety upon use thereof.

In consequence, there is an increasing demand for development of a raw drug for magnetic particle-containing drugs which is capable of producing the magnetic particle-containing drugs for diagnosis and therapies which can exhibit excellent stability and retentivity in blood and further can form a peculiar compatible bond to specific target molecules in view of tumor deposition, with a good reproducibility.

PRIOR DOCUMENTS

Patent Documents

Patent Document 1: Japanese Patent Application Laid-Open (KOKAI) No. 3-128331
Patent Document 2: Japanese Patent Application Laid-Open (KOKAI) No. 4-52202
Patent Document 3: Japanese Patent Application Laid-Open (KOKAI) No. 7-122410
Patent Document 4: Japanese Patent Application Laid-Open (TOKUHYO) No. 8-500700
Patent Document 5: Japanese Patent Application Laid-Open (KOKAI) No. 11-106391
Patent Document 6: Japanese Patent Application Laid-Open (KOKAI) No. 1-4002
Patent Document 7: Japanese Patent Application Laid-Open (KOKAI) No. 5-310429
Patent Document 8: Japanese Patent Application Laid-Open (KOKAI) No. 2006-28032
Patent Document 9: Japanese Patent Application Laid-Open (KOKAI) No. 2003-112925
Patent Document 10: PCT Pamphlet WO 95/31220
Patent Document 11: Japanese Patent No. 4079996

SUMMARY OF THE INVENTION

Problems to be Solved by the Invention

As described above, in order to produce magnetic material-containing drugs having uniform properties with a good reproducibility, it is essentially required that the biocompatible substance and the magnetic iron oxide fine particles are uniformly dispersed and mixed. For this purpose, it is also required that the magnetic iron oxide fine particles in the raw drug is present in the form of a monodisperse colloid aqueous solution comprising the magnetic iron oxide fine particles having a fine uniform particle diameter.

In addition, in order to maintain a good stability in blood, it is required that the magnetic iron oxide fine particles have a good dispersion stability in a neutral pH range.

Further, it is required that the magnetic particles are provided on a surface thereof with a functional group to form a strong bond to vital molecules such as antibodies.

Furthermore, it has been demanded to provide magnetic iron oxide fine particles (dried particles) which are capable of exhibiting a high oxidation resistance and being re-dispersed with a desired concentration at a desired time.

The present invention has been attained to solve the above conventional problems. A technical object of the present invention is to provide a dispersed colloid aqueous solution comprising magnetic iron oxide fine particles having a uniform particle size whose surface is modified with a carboxyl group-containing polymer, and the magnetic iron oxide fine particles which are capable of readily preparing the dispersed colloid aqueous solution.

Means for Solving the Problems

That is, according to the present invention, there is provided a magnetic particle-containing water dispersion comprising magnetic iron oxide fine particles which have a primary particle diameter of 5 to 15 nm and an average secondary particle diameter of 10 to 60 nm, a surface of the respective magnetic iron oxide fine particles being coated with a carboxyl group-containing polymer (Invention 1).

Also, according to the present invention, there is provided the above magnetic particle-containing water dispersion wherein the water dispersion has a zeta potential of not more than −20 mV when a pH value of the water dispersion lies within the range of 6 to 8 (Invention 2).

Also, according to the present invention, there is provided the above magnetic particle-containing water dispersion wherein the carboxyl group-containing polymer is a polyacrylic acid having a molecular weight of 1500 to 10000 (Invention 3).

In addition, according to the present invention, there is provided a process for producing the magnetic particle-containing water dispersion as described in any one of the above Inventions, comprising the steps of:

heating an aqueous solution in which the carboxyl group-containing polymer is dissolved, to a temperature of 90 to 100° C. in a nitrogen atmosphere;

adding a solution of a ferrous (II) salt and a ferric (III) salt and an alkali solution to the aqueous solution to react with each other at the same temperature;

cooling the resulting solution to room temperature and then adding ethanol to the solution to obtain a precipitate; and removing a supernatant liquid from the solution, and then dispersing the precipitate in water and subjecting the resulting dispersion to dialysis to obtain a water dispersion comprising the magnetic iron oxide fine particles whose surface is coated with the carboxyl group-containing polymer (Invention 4).

Also, according to the present invention, there is provided the above process for producing the magnetic particle-containing water dispersion wherein a molar ratio of a carboxyl group (COOH) to whole iron (Fe) (COOH/Fe) upon the reaction is 0.3 to 3 (Invention 5).

Effect of the Invention

The magnetic iron oxide fine particles according to the present invention can be readily dispersed in water to form a dispersed colloid of the magnetic iron oxide fine particles.

The magnetic particle-containing water dispersion according to the present invention is in the form of a dispersed colloid aqueous solution comprising finely divided magnetic iron oxide fine particles, and further the surface of the respective magnetic iron oxide fine particles is coated with a carboxyl group-containing polymer. Therefore, it is possible to readily produce drugs comprising a composite material formed by uniformly dispersing the magnetic iron oxide fine particles in a biocompatible substance. In addition, since the raw drug comprises no liquid medium such as a surfactant, there is caused a less adverse influence on safety in living organisms.

In addition, when the finely divided magnetic particles are formed into an aggregated state thereof in a pharmaceutical drug granulating step, the obtained granulated particles are imparted with a function as a ferromagnetic material.

Also, the magnetic particles are in the form of ultrafine particles and therefore can be readily excreted from living organisms after dosage thereof.

BEST MODE FOR CARRYING OUT THE INVENTION

The construction of the present invention is described in detail below.

The primary particles of the magnetic iron oxide fine particles according to the present invention have an average particle diameter of 5 nm to 15 nm. When the average particle diameter of the primary particles of the magnetic iron oxide fine particles is less than 5 nm, the resulting particles tend to be non-crystalline or amorphous. When the average particle diameter of the primary particles of the magnetic iron oxide fine particles is more than 15 nm, the resulting particles tend to have an excessively large coercive force and suffer from excessive magnetic aggregation, so that secondary particles thereof have a particle diameter of not less than 200 nm. The average particle diameter of the primary particles of the magnetic iron oxide fine particles is preferably from 5 to 12 nm and more preferably not more than 10 nm since the particles can suitably exhibit a low coercive force.

The secondary particles of the magnetic iron oxide fine particles according to the present invention have an average particle diameter of 10 nm to 60 nm. When the average particle diameter of the secondary particles of the magnetic iron oxide fine particles is less than 10 nm, the resulting particles tend to be deteriorated in heat generation by an alternating magnetic field when used in thermotherapy for cancers. On the other hand, when the average particle diameter of the secondary particles of the magnetic iron oxide fine particles is more than 60 nm, there tends to arise such a problem that the resulting particles are hardly excreted from living organisms after dosage thereof. The average particle diameter of the secondary particles of the magnetic iron oxide fine particles is preferably 10 nm to 30 nm.

The magnetic iron oxide fine particles according to the present invention are in the form of a spinel type ferromagnetic material represented by the compositional formula: $MO \cdot Fe_2O_3$ wherein M is a divalent metal. When M in the above formula is Fe, the magnetic iron oxide fine particles have a compositional formula of $xFeO \cdot Fe_2O_3$ wherein x represents a content of the divalent iron. When x is 1 (x=1), the compositional formula is $FeO \cdot Fe_2O_3$, i.e., the magnetic particles are magnetite, whereas when x is 0 (x=0), the compositional formula is $g\text{-}Fe_2O_3$, i.e., the magnetic particles are maghemite. When x is intermediate between 0 and 1 (x=0 to 1), the spinel type iron oxide is magnetic iron oxide. These superparamagnetic iron oxide particles are suitably used in the present invention.

In the magnetic iron oxide fine particles of the present invention which are represented by the compositional formula of $MO \cdot Fe_2O_3$ wherein M is a divalent metal, as the divalent metal M, Mg may also be selected in addition to Fe. This is because Mg has a biocompatibility. In addition, the other divalent metals may also be selectively used according to the applications of the magnetic particles.

The magnetic iron oxide fine particles according to the present invention are preferably in the form of a superparamagnetic material, and preferably have a coercive force of 0 to 6.0 kA/m. When the coercive force of the magnetic iron oxide fine particles is more than 6.0 kA/m, the particles tend to generate residual magnetization and therefore tend to be magnetically aggregated together. The coercive force of the magnetic iron oxide fine particles is more preferably 0.05 to 4.0 kA/m. The magnetic iron oxide fine particles according to the present invention have a saturation magnetization (ss) of 5 to 90 $Am^2$/kg. When the saturation magnetization (ss) of the magnetic iron oxide fine particles is less than 5 $Am^2$/kg, the particles tend to have poor magnetic properties. Whereas, it may be difficult to obtain spinel type iron oxide particles having a magnetization value of more than 90 $Am^2$/kg. The saturation magnetization (ss) of the magnetic iron oxide fine particles is preferably 10 to 85 $Am^2$/kg.

Examples of the carboxyl group-containing polymer used in the present invention include many kinds of polymers such as polyacrylic acids, polymethacrylic acids and polyamino acids. Among these polymers, preferred are polyacrylic acids in view of a particle size and a particle size distribution of the resulting magnetic iron oxide fine particles.

The carboxyl group-containing polymer preferably has a molecular weight of 1500 to 10000. When the molecular weight of the carboxyl group-containing polymer is less than 1500, the resulting magnetic particles tend to have an excessively large primary particle diameter. On the other hand, when the molecular weight of the carboxyl group-containing polymer is more than 10000, the magnetic particles tend to be aggregated together, so that the secondary particles thereof tend to have a large particle diameter.

The magnetic particle-containing water dispersion according to the present invention has a zeta potential of not more than −20 mV when a pH value of the water dispersion lies in the range of 6 to 8. In view of a biocompatibility, when the zeta potential of the water dispersion as measured when the pH value thereof lies within the range of 6 to 8 is more than −20 mV, the resulting particles tend to have problems such as poor stability with time.

The isoelectric point of the magnetic particle-containing water dispersion according to the present invention is preferably 2.0 to 3.0.

The concentration of the magnetic iron oxide fine particles in the magnetic particle-containing water dispersion according to the present invention is preferably 5 to 50 mg/mL. When the concentration of the magnetic iron oxide fine particles in the water dispersion is more than 50 mg/mL, since a van der Waals force acting between the particles tends to become too large, the particles tend to be undesirably readily aggregated together. When the concentration of the magnetic iron oxide fine particles in the water dispersion is less than 5 mg/mL, such a thin water dispersion tends to be unpractical. The concentration of the magnetic iron oxide fine particles in the magnetic particle-containing water dispersion is more preferably 10 to 40 mg/mL.

The magnetic iron oxide fine particles according to the present invention may be in the form of a composite material comprising, in addition to the magnetic particles, phospholipids, polysaccharides, proteins or dextrins.

Next, the process for producing the magnetic particle-containing water dispersion according to the present invention is described.

The magnetic iron oxide fine particles according to the present invention can be synthesized by an aqueous solution reaction (also referred to as a wet method) using an iron salt aqueous solution and an alkali aqueous solution.

In general, the aqueous solution reaction may be frequently carried out by a co-precipitation method and an oxidation reaction method.

The co-precipitation method is the reaction in which when an alkali aqueous solution is added to a mixed aqueous solution comprising 1 mol of a ferrous (Fe(II)) salt aqueous solution and 2 mol of a ferric (Fe(III)) salt aqueous solution while stirring, the Fe(II) and 2Fe(III) are subjected to co-precipitation reaction therebetween to produce magnetite particles which are in the form of black spinel type magnetic iron oxide. In this reaction, for example, if Mg as the divalent metal other than Fe is added, Mg-containing spinel type magnetic iron oxide fine particles are produced. In addition, the size of the particles produced by the above reaction can be controlled by varying reaction conditions such as concentrations of the iron salts and a mixing temperature. Therefore, by using suitable combination of these reaction conditions, it is possible to produce magnetic iron oxide fine particles having a desired particle size.

Even though a polyacrylic acid aqueous solution is added and reacted in the course of the above reaction, it is not possible to prepare the magnetic particle-containing water dispersion comprising the magnetic iron oxide fine particles having a particle size distribution as aimed by the present invention.

On the other hand, the oxidation reaction method is the reaction in which an alkali aqueous solution is added to a ferrous salt aqueous solution to produce a ferrous hydroxide colloid, and then an oxygen-containing gas such as air is passed through the ferrous hydroxide colloid-containing aqueous solution while heating and stirring to subject the ferrous hydroxide colloid to oxidation reaction, thereby producing magnetite particles as black magnetic iron oxide. Similarly to the above co-precipitation method, if the divalent metal other than Fe is added, spinel iron oxide particles comprising the metal added are obtained. In addition, by using suitable combination of these reaction conditions and suitably controlling the reaction conditions, it is possible to produce desired magnetic iron oxide fine particles.

However, in the case where the oxidation reaction of the above ferrous salt is carried out in the presence of a polyacrylic acid, even when a polyacrylic acid aqueous solution is added and reacted in the course of the above reaction, it is not possible to prepare the magnetic particle-containing water dispersion comprising the magnetic iron oxide fine particles having a particle size distribution as aimed by the present invention. Further, the oxidation reaction tends to proceed excessively in the course of the purification treatment, so that the color of the resulting particles is not black as a color of magnetite, but tends to be tinted with yellow to brown.

In consequence, as a result of the present inventors' earnest study to solve the above problems, the following reaction conditions have been found.

That is, an aqueous solution in which the carboxyl group-containing polymer such as a polyacrylic acid is dissolved is heated to a predetermined temperature, and then a mixed aqueous solution comprising the ferrous salt and the ferric salt and an alkali aqueous solution such as an aqueous ammonia solution are quickly added to the above solution to react with each other. When the magnetic iron oxide fine particles are produced through the above reaction, it is considered that the polyacrylic acid coat is formed immediately on the surface of the respective magnetite particles produced by the reaction so that aggregation between the particles can be prevented.

Examples of the ferrous salt aqueous solution used in the present invention include a ferrous sulfate aqueous solution, a ferrous chloride aqueous solution and the like. Examples of the ferric salt aqueous solution used in the present invention include a ferric sulfate aqueous solution, a ferric chloride aqueous solution and the like.

Examples of the alkali aqueous solution used in the present invention include an aqueous ammonia, aqueous solutions of alkali metal hydroxides such as sodium hydroxide and potassium hydroxide, and aqueous solutions of alkali earth metal hydroxides such as magnesium hydroxide and calcium hydroxide. Among these alkali aqueous solutions, the aqueous ammonia is preferably used.

In the present invention, the alkali aqueous solution may be added in an equivalent amount based on the ferrous iron and the ferric iron.

In the present invention, it is important that upon the reaction of the magnetic iron oxide fine particles, the carboxyl group-containing polymer such as a polyacrylic acid is previously dissolved in the reaction solution. When the carboxyl group-containing polymer is allowed to be previously present in the reaction solution, the surface of the respective magnetite particles produced by the reaction is immediately coated with the polyacrylic acid, so that aggregation between the particles can be prevented.

The concentration of the carboxyl group-containing polymer being present in the reaction solution may be adjusted such that a molar ratio of the polymer to whole iron (Fe) in the reaction solution is 0.3 to 3.0. When the concentration of the polymer is less than 0.3, the concentration of the polymer tends to be too dilute, so that the magnetic iron oxide fine particles may fail to be coated with the polymer to such an extent that aggregation between the particles can be prevented. When the concentration of the polymer is more than 3.0, the effect of addition of the polymer tends to be saturated, and the use of such a high concentration of the polymer is therefore meaningless. The concentration of the carboxyl group-containing polymer is preferably 0.8 to 2.5 in terms of a molar ratio to the whole Fe. When the concentration of the carboxyl group-containing polymer is adjusted to the above specific range, it is possible to control a zeta potential of the water dispersion to not more than −20 mV.

The reaction temperature used in the present invention is preferably in the range of 90 to 100° C. When the reaction temperature is lower than 90° C., goethite tends to be included in the resulting particles. Even when the reaction temperature is higher than 100° C., magnetite particles may be produced, but such a high reaction temperature tends to need use of a special apparatus such as an autoclave, resulting in industrially disadvantageous process.

In the present invention, the magnetic particle-containing water dispersion is washed with water in the following manner. That is, the solution obtained after the reaction is cooled to room temperature and then transferred into a beaker, etc., and an almost equal amount of ethanol is added to the reaction solution while stirring until producing a precipitate. After removing a supernatant liquid from the reaction solution, ion-exchanged water is added to the precipitate to disperse the precipitate therein. Ethanol is added again to the resulting dispersion, and then the dispersion is subjected to centrifugal separation to remove a supernatant liquid therefrom. The above procedure is repeated, and the finally obtained precipitate is dispersed in ion-exchanged water. If required, the resulting water dispersion is concentrated using an evaporator.

Next, the water dispersion is subjected to dialysis using a dialysis membrane in order to remove water-solubilized salts therefrom. After concentrating the dispersion using an evaporator, a supernatant liquid is recovered using a centrifugal separator to remove the remaining aggregated particles therefrom.

Next, the magnetic particle-containing water dispersion recovered as the supernatant liquid is allowed to stand in a refrigerator maintained at a temperature of −20° C. or lower for 5 hr or longer and thereby frozen, and the thus frozen product is freeze-dried under reduced pressure to obtain magnetic iron oxide fine particles according to the present invention.

The above magnetic particle-containing water dispersion is further diluted to control a concentration thereof to 5 to 50 mg/mL, thereby obtaining a magnetic particle-containing water dispersion in which the magnetic iron oxide fine particles are dispersed in ion-exchanged water.

Further, the thus obtained magnetic iron oxide fine particles may also be combined with phospholipids, polysaccharides, proteins or dextrins to form a composite material thereof. The thus obtained composite material can be used in various applications. For example, the composite material may be used in DDS as a method for delivering drugs, CT diagnosis used in roentgen and MRI (magnetic resonance imaging system), and various therapies such as thermotherapy.

<Function>

As a result of the present inventors' earnest study, it has been found that the magnetic particle-containing water dispersion comprising superparamagnetic iron oxide fine particles whose surface is coated with the carboxyl group-containing polymer can be stably dispersed under the specific conditions as described herein.

A material capable of exhibiting a superparamagnetism is a ferromagnetic material having no coercive force (zero coercive force). That is, the large ferromagnetic particles even having a single domain structure will undergo occurrence of residual magnetization after applying an external magnetic field to magnetize the particles and then releasing the magnetic field therefrom. However, when the particle diameter of the ferromagnetic particles is reduced until ultrafine particles, the coercive force thereof is reduced and finally reaches zero. As a result, although the particles are magnetized when applying an external magnetic field thereto, any residual magnetization is not generated after releasing the magnetic field therefrom. This phenomenon is caused by thermal agitation effect, and the ferromagnetic fine particles having such an effect are called superparamagnetic particles.

The magnetic particle-containing water dispersion according to the present invention is free from aggregation therebetween even when approaching to a permanent magnet having a surface magnetic flux of 10 mT (100 gauss), and is present in the form of a monodisperse colloid aqueous solution which can be stably maintained for a long period of time. It seems that such a phenomenon is contradictory to the fact that the magnetic iron oxide fine particles are in the form of a ferromagnetic material having a saturation magnetization as large as 50 to 90 $Am^2/kg$. However, the saturation magnetization represents the magnetization value not per one particle but per unit weight as measured with respect to the magnetic iron oxide fine particles in the form of a powder. Therefore, the total number of particles per unit weight is increased as the particles becomes finer, so that the magnetization value per one particle becomes smaller.

In addition, the reason why the magnetic iron oxide fine particles are used as the magnetic particles is that the iron oxide has a good biocompatibility, and the finer particles can be more readily excreted from living organisms.

EXAMPLES

Next, the present invention is described in more detail by the following Examples. However, these Examples are only illustrative and not intended to limit the invention thereto. In the following, the evaluation methods used in the following Examples, etc., are explained.

Meanwhile, the structural analysis of the obtained product was carried out using an X-ray diffractometer.

The particle size distribution was observed using a transmission electron microscope (TEM). Further, the average particle diameter of primary particles was determined by analysis using a digitizer.

The average particle diameter of secondary particles was measured by a dynamic light scattering method using a particle size distribution measuring device "FPAR-1000" manufactured by Otsuka Electronics Co., Ltd.

The specific surface area was measured by BET method.

The magnetic properties of the particles were measured using a vibration sample type magnetometer "VSM" by applying a magnetic field of 796 kA/m (10 kOe) thereto.

The zeta potential and isoelectric point were measured using "ELS-6000" manufactured by Otsuka Electronics Co., Ltd.

Example 1

A 1000 mL reaction container equipped with a stirrer and a heater was used. In addition, raw iron salt materials and sodium hydroxide used therein both were guaranteed reagents, and ion-exchanged water was used as water.

(1) Synthesis Step of Magnetic Iron Oxide Fine Particles:

The reaction container was charged with 7.83 g of polyacrylic acid having a molecular weight of 5000 and 713.2 mL of ion-exchanged water, and while blowing a nitrogen gas into the reaction container, the contents of the reaction container were heated as such to 95° C. Next, 10 mL of a 1.6 mmol/L ferrous sulfate aqueous solution and 10 mL of a 3.2 mmol/L ferric chloride aqueous solution were charged into the reaction container (COOH/Fe ratio: 2.27), and further 59.4 mL of a 14.8 mmol/L aqueous ammonia were added to the reaction container. The contents of the reaction container were reacted with each other for 2 hr while stirring. The resulting aqueous solution was cooled to 65° C. The obtained reaction solution was concentrated using an evaporator to reduce its volume to about 100 mL. The concentrated reaction solution was cooled to room temperature and then transferred to beaker, and ethanol was added in an almost equal amount thereto while stirring by a stirrer until producing a precipitate. After removing a supernatant liquid from the reaction solution, ion-exchanged water was added to the remaining precipitate such that the total amount of the resulting mixture was about 100 g, and the mixture was dispersed while stirring. Then, ethanol was added again in an equal amount to the dispersion, and the resulting dispersion was treated using a centrifugal separator at 1000 rpm for 10 min. After removing a supernatant liquid from the obtained reaction solution, the above procedure was repeated again, and the finally obtained precipitate was dispersed in ion-exchanged water. Further, the resulting dispersion was concentrated using an evaporator to reduce its weight to about 40 g.

A part of the thus obtained colloid aqueous solution was sampled and subjected to water-washing and filtration to obtain a paste. The thus obtained paste was freeze-dried to obtain particles. As a result of analyzing the thus obtained particles, it was confirmed that the particles had a BET specific surface area of 230 m$^2$/g, an average primary particle diameter of 5 nm as measured by TEM, and an average secondary particle diameter of 17.3 nm as measured by a dynamic light scattering method. Further, it was confirmed that the obtained particles were magnetic iron oxide fine particles having magnetic properties including a saturation magnetization (ss) of 13 Am$^2$/kg and a coercive force (Hc) of 0.35 kA/m.

(2) Purification Step of Dispersed Particles:

The particles were purified using a dialysis membrane. The resulting dialyzate was concentrated using an evaporator to reduce its volume to 200 mL, and the concentrated solution was subjected to centrifugal separation at 12000 G for 30 min to recover a supernatant liquid therefrom. In the above procedure, aggregated particles were removed. Thus, the black colloid aqueous solution was purified.

As a result, it was confirmed that the concentration of the thus obtained magnetic particle-containing water dispersion was 10 mg/mL, and the pH value of the magnetic particle-containing water dispersion was 6.5. Further, it was confirmed that the zeta potential of the water dispersion was −34 mV as measured at a pH of 7.0, and the isoelectric point thereof was 2.5.

Example 2

The reaction was conducted in the same manner as defined in Example 1 except for using a polyacrylic acid having a molecular weight of 1800, thereby obtaining a colloid solution. As a result of analyzing the resulting particles in the same manner as define in Example 1, it was confirmed that the particles had a BET specific surface area of 165 m$^2$/g, an average primary particle diameter of 7 nm as measured by TEM, and an average secondary particle diameter of 56 nm as measured by a dynamic light scattering method. Further, it was confirmed that the obtained particles were magnetic iron oxide fine particles having magnetic properties including a saturation magnetization (ss) of 32 Am$^2$/kg and a coercive force (Hc) of 0.65 kA/m.

Next, the dispersed particles were subjected to purification step in the same manner as defined in Example 1, thereby obtaining a magnetic particle-containing water dispersion.

As a result, it was confirmed that the concentration of the thus obtained magnetic particle-containing water dispersion was 10 mg/mL, and the pH value of the magnetic particle-containing water dispersion was 6.5. Further, it was confirmed that the zeta potential of the water dispersion was −31 mV as measured at a pH of 7.0, and the isoelectric point thereof was 2.6.

Comparative Example 1

A 1000 mL flask was charged with an aqueous solution previously prepared by mixing 60 g of a 13.9 mol/L NaOH aqueous solution with 530 g of ion-exchanged water and then heating the resulting mixture to 80° C. Then, 108.4 g of a 0.8 mmol/L ferrous chloride aqueous solution and 80 g of a 2.5 mmol/L ferric chloride aqueous solution were mixed with and added to the aqueous solution previously charged into the flask. Next, the flask was charged with 60 g of an aqueous solution in which 12.1 g of a polyacrylic acid having a molecular weight of 5000 were dissolved, and the contents of the flask were reacted with each other at the same temperature for 1 hr. Thereafter, ion-exchanged water was added to the flask, and a supernatant liquid was removed by decantation from the reaction solution. This procedure was repeated to remove water-solubilized salts from the dispersion.

A part of the thus obtained magnetic particle-containing dispersion was sampled and subjected to water-washing and filtration to obtain a paste. The thus obtained paste was freeze-dried to obtain particles. As a result of analyzing the thus obtained particles, it was confirmed that the particles had a BET specific surface area of 176 m$^2$/g, an average primary particle diameter of 8 nm as measured by TEM, and an average secondary particle diameter of 120 nm as measured by a dynamic light scattering method. Thus, the obtained particles were apparently in the form of aggregated particles. Further, it was confirmed that the obtained particles had magnetic properties including a saturation magnetization (ss) of 26.3 Am$^2$/kg and a coercive force (Hc) of 0.92 kA/m.

Next, the dispersed particles were subjected to purification step in the same manner as defined in Example 1, thereby obtaining a magnetic particle-containing water dispersion.

As a result, it was confirmed that the concentration of the thus obtained magnetic particle-containing water dispersion was 10 mg/mL, and the pH value of the magnetic particle-containing water dispersion was 7.3. Further, it was confirmed that the zeta potential of the water dispersion was −12 mV as measured at a pH of 7.0, and the isoelectric point thereof was 5.2.

Comparative Example 2

A 300 mL flask was charged with 50 mL of a 0.1 mol/L ferrous chloride aqueous solution and then with 0.09 g of a polyacrylic acid having a molecular weight of 1800. Next, 11 mL of a 0.7 mol/L KOH aqueous solution was added to the flask to produce a precipitate of iron hydroxide. Then, 50 mL of an aqueous solution comprising 0.035 mL of hydrogen peroxide was added to the flask at a rate of 33 mL/h. The contents of the flask were reacted with each other for 2 hr, and then ion-exchanged water was added thereto to subject the resulting dispersion to decantation. The above decantation was repeated to remove water-solubilized salts therefrom.

A part of the thus obtained magnetic particle-containing dispersion was sampled and subjected to water-washing and filtration to obtain a paste. The thus obtained paste was freeze-dried to obtain particles. As a result of analyzing the thus obtained particles, it was confirmed that the particles had a BET specific surface area of 176 m$^2$/g. On the other hand, as a result of observing the particles using TEM, it was confirmed that the particles were in the form of a mixture of spherical particles and many acicular particles having an average primary particle diameter of 10 to 50 nm, and had an average secondary particle diameter of 120 nm as measured by a dynamic light scattering method. Thus, the obtained particles were apparently in the form of aggregated particles. Further, it was confirmed that the obtained particles had magnetic properties including a saturation magnetization (ss) of 26.3 Am$^2$/kg and a coercive force (Hc) of 0.92 kA/m.

Next, the dispersed particles were subjected to purification step in the same manner as defined in Example 1, thereby obtaining a magnetic particle-containing water dispersion.

As a result, it was confirmed that the concentration of the thus obtained magnetic particle-containing water dispersion was 10 mg/mL, and the pH value of the magnetic particle-containing water dispersion was 6.1. Further, it was confirmed that the zeta potential of the water dispersion was 3 mV as measured at a pH of 7.0, and the isoelectric point thereof was 6.2.

INDUSTRIAL APPLICABILITY

The magnetic particle-containing water dispersion according to the present invention comprises magnetic fine particles whose surface is modified with a carboxyl group-containing polymer. Therefore, it is possible to readily produce a drug in the form of a composite material prepared by uniformly dispersing the magnetic fine particles in a biocompatible substance. In addition, since the zeta potential of the water dispersion is not more than −20 mV when the pH value of the water dispersion lies in a neutral range of from 6 to 8, the magnetic particles therein hardly suffer from aggregation therebetween even within living organisms and can exhibit a high stability with time. Further, since the primary particle diameter and secondary particle diameter of the magnetic fine particles are very small, the finally obtained particles are prevented from excessively increasing in diameter even though the surface of the respective particles is modified with antibody, etc. Thus, the magnetic fine particles of the present invention can be readily excreted from human body even after dosage thereto. Accordingly, it is possible to provide a raw drug which is free from any problems with respect to safety after dosage to human body as well as metabolism and excretion.

The invention claimed is:

1. A process for producing magnetic iron oxide fine particles,
    the magnetic iron oxide fine particles having a primary particle diameter of 5 to 15 nm and an average secondary particle diameter of 10 to 60 nm, a surface of the respective magnetic iron oxide fine particles being coated with a carboxyl group-containing polymer,
    the process comprising the steps of:
    heating an aqueous solution in which the carboxyl group-containing polymer is dissolved, to a temperature of 90 to 100° C. in a nitrogen atmosphere;
    adding a solution of a ferrous (II) salt and a ferric (III) salt and an alkali solution to the aqueous solution to react with each other at the same temperature;
    adding ethanol to the resulting solution to obtain a precipitate;
    removing a supernatant liquid from the solution, and then dispersing the precipitate in water and subjecting the resulting dispersion to dialysis to obtain a water dispersion comprising the magnetic iron oxide fine particles whose surface is coated with the carboxyl group-containing polymer; and
    freeze-drying the water dispersion to obtain the magnetic iron oxide fine particles.

2. A process for producing a magnetic particle-containing water dispersion,
    the magnetic particle-containing water dispersion comprising water and magnetic iron oxide fine particles dispersed in the water, which magnetic iron oxide fine particles have an average primary particle diameter of 5 to 15 nm and an average secondary particle diameter of 10 to 60 nm, a surface of the respective magnetic iron oxide fine particles being coated with a carboxyl group-containing polymer,
    the process comprising the steps of:
    heating an aqueous solution in which the carboxyl group-containing polymer is dissolved, to a temperature of 90 to 100° C. in a nitrogen atmosphere;
    adding a solution of a ferrous (II) salt and a ferric (III) salt and an alkali solution to the aqueous solution to react with each other at the same temperature;
    cooling the resulting solution to room temperature and then adding ethanol to the solution to obtain a precipitate; and
    removing a supernatant liquid from the solution, and then dispersing the precipitate in water and subjecting the resulting dispersion to dialysis to obtain a water dispersion comprising the magnetic iron oxide fine particles whose surface is coated with the carboxyl group-containing polymer.

3. A process for producing the magnetic particle-containing water dispersion according to claim 1, wherein a molar ratio of a carboxyl group (COOH) to whole iron (Fe)(COOH/Fe) upon the reaction is 0.3 to 3.

* * * * *